(12) United States Patent
Radl et al.

(10) Patent No.: US 7,282,517 B2
(45) Date of Patent: Oct. 16, 2007

(54) METHOD OF MANUFACTURING GLIMEPIRIDE AND THE RESPECTIVE INTERMEDIATE

(75) Inventors: Stanislav Radl, Praha 2 (CZ); Kamal Jarrah, Praha 10 (CZ)

(73) Assignee: Zentiva, a.s., Praha (CZ)

(*) Notice: Subject to any disclaimer, the term of this patent is extended or adjusted under 35 U.S.C. 154(b) by 162 days.

(21) Appl. No.: 10/546,238

(22) PCT Filed: Feb. 20, 2004

(86) PCT No.: PCT/CZ2004/000009

§ 371 (c)(1),
(2), (4) Date: Aug. 22, 2005

(87) PCT Pub. No.: WO2004/073585

PCT Pub. Date: Sep. 2, 2004

(65) Prior Publication Data

US 2007/0054954 A1    Mar. 8, 2007

(30) Foreign Application Priority Data

Feb. 21, 2003    (CZ) .............................. PV 2003-530

(51) Int. Cl.
*A61K 31/4015*    (2006.01)
*C07D 207/28*    (2006.01)
(52) U.S. Cl. ...................... 514/423; 548/534
(58) Field of Classification Search ................ 514/423; 548/534
See application file for complete search history.

(56) References Cited

FOREIGN PATENT DOCUMENTS

EP    0 031 058    7/1981

OTHER PUBLICATIONS

Chinese Journal of Medicinal Chemistry, vol. 10(2), pp. 134-137 (2000).*
Deng, Yong et al: "Studies on synthetic process of glimepiride, new hypoglycemic agent", Chinese Journal of Medicinal Chemistry, vol. 10, No. 2, pp. 134-137, Jun. 2000, XP008033170.
Weyer, R. et al: "Acylureidoalkylphenylsulfonylureas with blood glucose lowering efficacy", Arzneimittel-Forschung, vol. 38, No. 8, pp. 1079-1080, 1988, XP-001194548.
Shirahata, Akira et al: "Trans-4-methylcyclohexylamine, a potent new inhibitor of spermidine synthase", Chemical & Pharmaceutical Bulletin, vol. 36, No. 8, pp. 3220-3222, 1988, XP-002290042.

* cited by examiner

*Primary Examiner*—Kamal A. Saeed
(74) *Attorney, Agent, or Firm*—Oblon, Spivak, McClelland, Maier & Neustadt, P.C.

(57) ABSTRACT

A method of manufacturing glimepiride of formula I wherein trans-4-methylcyclohexylamine pivalate of formula VII is reacted, either directly or after conversion to trans-4-methylcyclohexylamine or to its another salt, with an alkyl [4-(2-{[(3-ethyl-4-methyl-2-oxo-2,5-dihydro-1H-pyrrol-1 yl)carbonyl]amino)ethyl)phenyl]-sulfonyl carbamate of general formula IV wherein R is a C1-C5 alkyl, giving glimepiride of formula I, trans-4-Methylcyclohexylamine pivalate of formula VII (I)

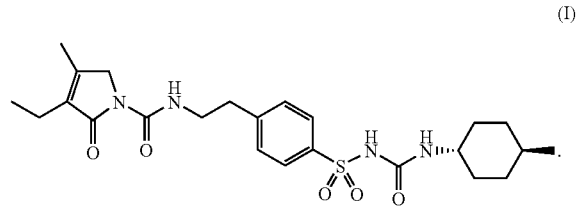

18 Claims, No Drawings

METHOD OF MANUFACTURING GLIMEPIRIDE AND THE RESPECTIVE INTERMEDIATE

TECHNICAL FIELD

This invention concerns trans-4-methylcyclohexylamine pivalate, its production and use for production of the antidiabetic glimepiride. trans-4-Methylcyclohexylamine pivalate is a novel, so far undisclosed, substance which can be, according to the present invention, preferably used for a synthesis of 1-(4-(2-(3-ethyl-4-methyl-2-oxo-3-pyrrolin-1-carboxamido)ethyl)phenylsulfonyl)-3-(trans-4-methylcyclohexyl)urea of formula I, known under the non-proprietary name glimepiride.

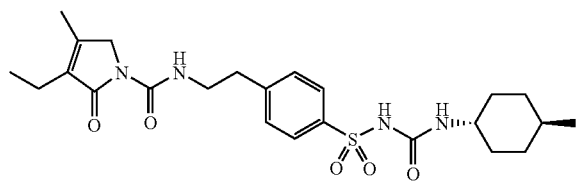
(I)

The mentioned medicament is a prominent representative of antidiabetic medicaments from the sulfonamide group.

BACKGROUND ART

Glimepiride is prepared according to the original patent EP 031 058 (U.S. Pat. No. 4,379,785) either via reaction of 3-ethyl-4-methyl-2-oxo-2,5-dihydro-pyrrol-1-carbox-[2-(4-sulfamoyl-phenyl)ethyl]-amide of formula II

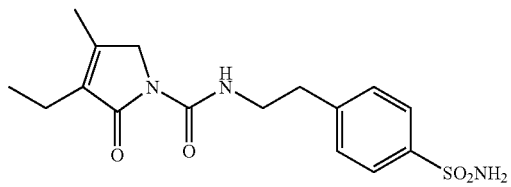
(II)

with trans-4-methylcyclohexylisocyanate of formula III

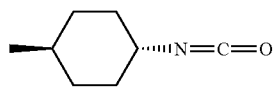
(III)

or via reaction of alkyl [4-(2-{[(3-ethyl-4-methyl-2-oxo-2,5-dihydro-1H-pyrrol-1-yl)carbonyl]amino}ethyl)phenyl]sulfonyl carbamate of formula IV

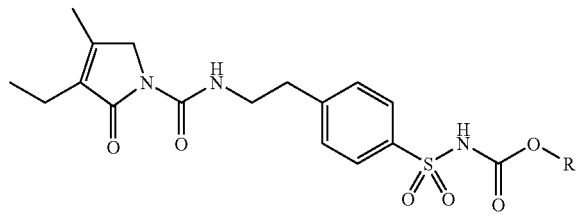
(IV)

wherein R is a $C_1$-$C_5$ alkyl, with trans-4-methylcyclohexylamine of formula V

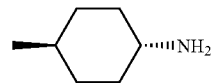
(V)

trans-4-Methylcyclohexylisocyanate of formula III is again prepared from trans-4-methylcyclohexylamine of formula V.

For the production of glimepiride, the key factor is sufficient purity of trans-4-methylcyclohexylamine of formula V with the lowest possible content of the cis-isomer. The most commonly used procedure is reduction of 4-methylcyclohexanoneoxime of formula VI

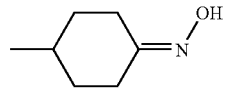
(VI)

with sodium in alcohols, most frequently in ethanol (T. P. Johnston, G. S. McCaleb, P. S. Opliger, W. R. Laster, J. A. Montgomery, J. Med. Chem. 1971, 14, 600-614). The amine obtained via this procedure typically contains between 8 to 10% of the cis-isomer (H. Booth, G. C. Gidley, P. R. Thornburrow, J. Chem. Soc. (B) 1971, 1047-1050). Further purification of the amine to a higher content of the trans-isomer via crystallization of its salts is not sufficiently documented. Earlier literature describes purification of crude trans-4-methylcyclohexylamine by crystallization of its hydrochloride, but in most cases neither yields nor the contents of the cis-isomer are given. The only rather detailed description of such purification is given in the above-mentioned paper (T. P. Johnston, G. S. McCaleb, P. S. Opliger, W. R. Laster, J. A. Montgomery, J. Med. Chem. 1971, 14, 600-614), wherein its authors have obtained, by triple crystallization in acetonitrile of the crude hydrochloride having the m.p. 250° C., a substance melting at 260° C., but in 27% yield.

DISCLOSURE OF INVENTION

This invention describes trans-4-methylcyclohexylamine pivalate of formula VII

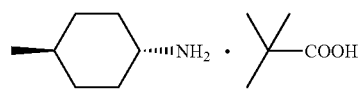
(VII)

with a high content of the trans-isomer and its direct use for production of glimepiride. The content of the cis-isomer has typically not exceeded 0.5% and the amine released from our samples has provided the hydrochloride meting typically at about 261° C.

The object of this invention is a method of manufacturing glimepiride of formula I

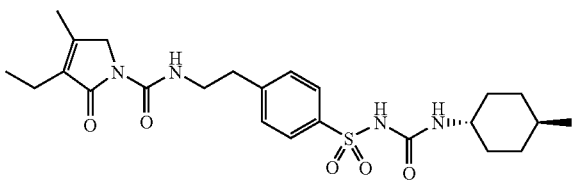

wherein trans-4-methylcyclohexylamine pivalate of formula VII

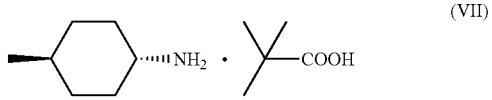

is reacted, either directly or after conversion to trans-4-methylcyclohexylamine or to its another salt, with an alkyl [4-(2-{[(3-ethyl-4-methyl-2-oxo-2,5-dihydro-1H-pyrrol-1-yl)carbonyl]amino}ethyl)phenyl]-sulfonyl carbamate of general formula IV

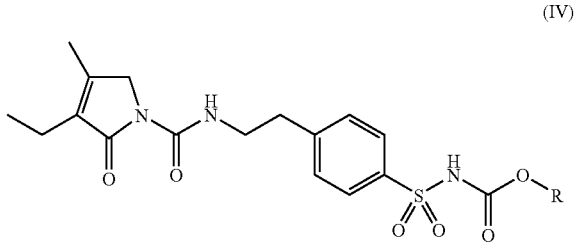

wherein R is a $C_1$-$C_5$ alkyl, giving glimepiride of formula I.

Another object of this invention is trans-4-methylcyclohexylamine pivalate of formula VII having a high content of the trans-isomer, which can be directly used for production of glimepiride. The whole procedure is based on a surprising finding that crude trans-4-methylcyclohexylamine of formula V with the content of up to 10% of the cis-isomer can be cleaned of the undesirable cis-isomer via conversion to the respective pivalate and crystallization from an appropriate solvent. Another surprising finding concerns the fact that this pivalate can be advantageously used for reaction with an alkyl [4-(2-{[(3-ethyl-4-methyl-2-oxo-2,5-dihydro-1H-pyrrol-1-yl)carbonyl]amino}ethyl)phenyl]sulfonyl carbamate of formula IV, wherein R is a $C_1$-$C_5$ alkyl, which leads to high yields of very pure glimepiride.

More detailed description of the invention follows.

trans-4-Methylcyclohexylamine pivalate of formula VII can be prepared from trans-4-methylcyclohexylamine, or alternatively from its salts, by reacting with pivalic acid or a salt thereof. For this purpose, one can use neutralization—a reaction of trans-4-methylcyclohexylamine with pivalic acid, displacement of the salt of the weak acid trans-4-methylcyclohexylamine with an acid or double substitution. In the invention, neutralization is preferred for its relative simplicity. However, all the other methods also lead to the purifying effect described below.

It has turned out that trans-4-methylcyclohexylamine hydrochloride obtained via the usual procedure, i.e. by reduction of 4-methylcyclohexanoneoxime of formula VI with sodium, decomposition of the reaction mixture with water and steam distillation with collecting into hydrochloric acid, which hydrochloride contains up to 10% of the cis-isomer, can be converted to pure trans-4-methylcyclohexylamine pivalate of formula VII with high content of the trans-isomer by a single crystallization or stirring in an appropriate solvent, subsequent conversion to the pivalate and further crystallization from an appropriate solvent. Appropriate solvents for crystallization of the crude hydrochloride turned out to be $C_1$-$C_5$ alcohols, their esters with $C_1$-$C_5$ acids or alternatively mixtures of the two, both anhydrous and with water content up to 50%, preferably up to 5%. Appropriate solvents for purification of pivalate proved to be cyclic $C_5$-$C_8$ hydrocarbons, especially advantageous being use of cyclohexane, aromatic hydrocarbons, especially advantageous being toluene, or mixtures of these solvents with addition of other co-solvents. One can use as co-solvents $C_1$-$C_5$ alcohols, their esters with $C_1$-$C_5$ acids, or alternatively mixtures of the two, both anhydrous and with water content up to 50%, preferably up to 5%.

trans-4-Methylcyclohexylamine pivalate of formula VII with high content of the trans-isomer obtained via this procedure can be converted to a base of trans-4-methylcyclohexylamine, or alternatively any salt thereof, using standard methods during which isomerization does not occur and the content of the trans isomer remains stable. However, the most advantageous is to use trans-4-methylcyclohexylamine pivalate of formula VII directly for preparation of glimepiride. The procedure is analogous to using a the free amine, i.e. an alkyl [4-(2-{[(3-ethyl-4-methyl-2-oxo-2,5-dihydro-1H-pyrrol-1-yl)carbonyl]amino}-ethyl)phenyl]sulfonyl carbamate of formula IV, wherein R is a $C_1$-$C_5$ alkyl, preferably methyl (R=Me) or ethyl (R=Et), is heated with trans-4-methylcyclohexylamine pivalate of formula VII in an appropriate solvent, e.g. in toluene or dioxan. In the usual procedure, the two starting substances were mixed with an appropriate solvent at lab temperature. With respect to the amount of the solvent, one can select from a wide range so that after the reaction is completed and the mixture is cooled down, crystals of the product fall out in high yields. Then, temperature is raised, according to the solvent used, to 40 up to 120° C., preferably to 70 up to 110° C. It is advantageous to use a solvent with boiling point within the mentioned range, e.g. toluene. At this increased temperature, the reaction is carried out for several hours. When an appropriate solvent is used in an appropriate amount high yield of very pure glimepiride falls out from the reaction mixture after it is cooled down.

However, originally used trans-4-methylcyclohexylamine of formula V converts easily to the carbonate on air and, in addition, it is difficult to handle. On the other hand, trans-4-methylcyclohexylamine pivalate of formula VII is a white to lightly yellowish, nonhygroscopic, crystalline substance stable on air. Contrary to trans-4-methylcyclohexylamine, the pivalate is without the typical amine smell.

In addition, in some cases, better yields and/or higher purity of the crude product were achieved. This invention further concerns purification of crude glimepiride. It can be achieved via crystallization from an appropriate solvent, e.g. dioxan, tetrahydrofuran, dimethoxyethane, diethoxymethane, acetic acid, dimethylsulfoxide, their mixture or a mixture with addition of acetone, acetonitrile, dimethylformamide.

Crystallization from these solvents yields a very efficient resource for final purification of crude glimepiride. On the other hand, it disadvantage is that heating in solvent can result in hydrolysis of the product which leads to creation of sulfonamide of formula II.

However, it has turned out that a sufficiently pure product can be obtained via stirring crude glimepiride, prepared from the mentioned intermediate products, in an appropriate organic solvent at lab temperature or a slightly higher one. Advantageous solvents for this stirring are dimethylsulfoxide, acetonitrile, acetone or toluene.

When the crude product is more contaminated it is appropriate to combine the two methods, i.e. after crystallization is performed the product is further purified via stirring.

With simultaneous application of purification of trans-4-methylcyclohexylamine via its pivalate of formula VII and further purification of crude glimepiride of formula I according to the invention, one can obtain exceptionally pure antidiabetic glimepiride with a content of the undesirable cis-isomer lower than 0.5%, even in case when the starting trans-4-methylcyclohexylamine contained up to 10% of the cis form.

The invention is explained in more detail in the following working examples. The examples, which illustrate preferred alternatives according to the invention, have a purely illustrative character and do not limit the extent of the invention in any respect.

EXAMPLES

Example 1 trans-4-Methylcyclohexylamine Pivalate (VII)

A solution of 1.50 kg of 4-methylcyclohexanonoxime (VI) in abs. ethanol (23.4 l) was heated to boiling and 2.88 kg of freshly cut sodium was added in small doses over the period of two hours. Then, the mixture was refluxed for another 2 hours and after cooling down, it was dissolved with water (29 l). The resulting mixture was distilled with steam, the distillate was collected in a mixture of water (1.8 l) and hydrochloric acid (1.8 l). The resulting acidic distillate was evaporated to dryness in an evaporator. The yield was 1,290 g of crude trans-4-methylcyclohexylamine hydrochloride (73%) with 91% content of the trans-isomer.

The crude product was further purified via stirring with ethylacetate (3 l) for 2 hours at lab temperature. After draining, 1,270 g of trans-4-methylcyclohexylamine hydrochloride were obtained which was dissolved in a minimal amount of water (2 l) and alkalized with sodium hydroxide (530 g). After separation of the top phase with the released trans-4-methylcyclohexylamine (V), the bottom phase was shaken out with dichloromethane. Dichloromethane was distilled off and the distillation residue was added to the first separated phase. The combined fractions of trans-4-methylcyclohexylamine were dissolved in methanol (3 l) and 858 g of pivalic acid were added to the resulting solution. Approximately 1,700 g of a crude product were obtained, which was dissolved in hexane (8 l) under boiling conditions. After 1 hour, the mixture was cooled down and white crystals that fell out were drained out. The yield was 1,670 g of trans-4-methylcyclohexylamine pivalate (VII) (66% yield calculated on the starting oxime (VI) with 99.6% content of the trans-isomer. Melting point 173-175° C. A small sample released from this sample has produced a hydrochloride having the melting point of 261.5-262° C.

Example 2 trans-4-Methylcyclohexylamine Pivalate (VII)

The procedure described in Example 1, wherein crystallization of the crude hydrochloride was performed from ethanol and that of the pivalate from the mixture of toluene and cyclohexane 1:3, yielded 59% of trans-4-methylcyclohexylamine pivalate (VII) with 99.5% content of the trans-isomer. Melting point 173-175° C.

Example 3 trans-4-Methylcyclohexylamine Pivalate (VII)

The procedure described in Example 1, wherein crystallization of the hydrochloride was performed from ethanol and ethylacetate and that of the pivalate from cyclohexane, yielded 63% of trans-4-methylcyclohexylamine pivalate (VII) with 99.5% content of the trans-isomer. Melting point 174-176° C.

Example 4 trans-4-Methylcyclohexylamine pivalate (VII)

The procedure described in Example 1, wherein pre-purification of the crude hydrochloride was performed via stirring with ethylacetate with 5% water content and crystallization of the pivalate was performed from cyclohexane, yielded 66% of trans-4-methylcyclohexylamine pivalate (VII) with 99.3% content of the trans-isomer. Melting point 173-175° C.

Example 5 trans-4-Methylcyclohexylamine Pivalate (VII)

The procedure described in Example 1, wherein crystallization of the crude hydrochloride was performed from 2-butanone and that of the pivalate from a mixture of toluene and heptane 1:1 yielded 53% of trans-4-methylcyclohexylamine pivalate (VII) with 99.4% content of the trans-isomer. Melting point 173-175° C.

Example 6 trans-4-Methylcyclohexylamine Pivalate (VII)

From 250 g of pure trans-4-methylcyclohexylamine hydrochloride with 99.5% content of the trans-isomer, trans-4-methylcyclohexylamine was released, which was converted to trans-4-methylcyclohexylamine pivalate (VII) via the procedure described in Example 1. The yield was 322 g (90%) of the product with 99.7% content of the trans-isomer. Melting point 173-176° C.

Example 7

Glimepiride 41.0 g of the pivalate VII was added to the stirred mixture of 70.0 g of ethyl [4-(2-{[(3-ethyl-4-methyl-2-oxo-2,5-dihydro-1H-pyrrol-1-yl)carbonyl]amino}ethyl)phenyl]sulfonyl carbamate (IV, R=Et) in toluene (840 ml) and the mixture was refluxed for 4 hours. After cooling down to 15° C., the solid fraction was drained out and washed with cold toluene. The yield was 74.5 g (92%) of the crude product with an HPLC content of 98.5%. The crude product was subsequently purified via triple boiling in toluene (820 ml) for 3 hours, subsequent cooling down and draining. The yield was 68.5 g of glimepiride (84%) with an HPLC content of 99.5% (99.7% of the trans-isomer). Melting point 206-207° C.

Example 8

The procedure described in Example 7, wherein methyl [4-(2-{[(3-ethyl-4-methyl-2-oxo-2,5-dihydro-1H-pyrrol-1-yl)carbonyl]amino}ethyl)phenyl]sulfonyl carbamate (IV, R=Me) was used as the starting substance, yielded 77% of the product with the melting point 205-206° C.

Example 9

The procedure described in Example 7, wherein dioxan was used as the solvent instead of toluene, yielded 76% of the product with the melting point 206° C.

Example 10

The procedure described in Example 7, wherein crude glimepiride was stirred with acetone, yielded 87% of the product with the melting point 205-207° C.

Example 11

The procedure described in Example 7, wherein crude glimepiride was crystallized from dioxan, yielded 81% of the product with the melting point 205-206° C.

Example 12

The procedure described in Example 7, wherein crude glimepiride was dissolved in tetrahydrofuran and subsequently precipitated with pentane, yielded 73% of the product with the melting point 205-206° C.

Example 13

The procedure described in Example 7, wherein crude glimepiride was crystallized from acetic acid, yielded 76% of the product with the melting point 205-207° C.

Example 14

The procedure described in Example 7, wherein crude glimepiride was crystallized from dimethylsulfoxide, yielded 68% of the product with the melting point 205-206° C.

Example 15

The procedure described in Example 7, wherein crude glimepiride was purified via repeated stirring with a mixture of dimethylsulfoxide and acetone at lab temperature, yielded 82% of the product with the melting point 204-205° C.

Example 16

The procedure described in Example 7, wherein crude glimepiride was purified via repeated stirring with the mixture of dimethylsulfoxide and acetonitrile at lab temperature, yielded 78% of the product with the melting point 206-207° C.

Example 17

The procedure described in Example 7, wherein crude glimepiride was purified via repeated stirring with the mixture of dimethylsulfoxide and acetonitrile at the temperature 50° C., yielded 74% of the product with the melting point 204-206° C.

Example 18

The procedure described in Example 7, wherein crude glimepiride was purified via repeated stirring with acetonitrile at the temperature 50° C., yielded 81% of the product with the melting point 205-206° C.

The invention claimed is:
1. A method of manufacturing glimepiride of formula 1

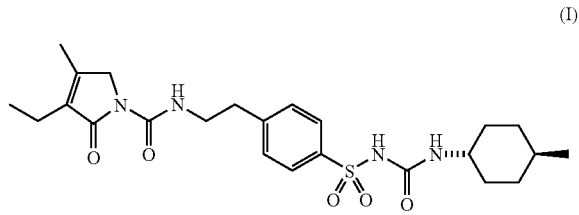

comprising reacting trans-4-methylcyclohexylamine pivalate of formula VII

with an alkyl [4-(2-{[(3-ethyl-4-methyl-2-oxo-2,5-dihydro-1H-pyrrol-1-yl)carbonyl]amino}ethyl)phenyl]-sulfonyl carbamate of general formula IV

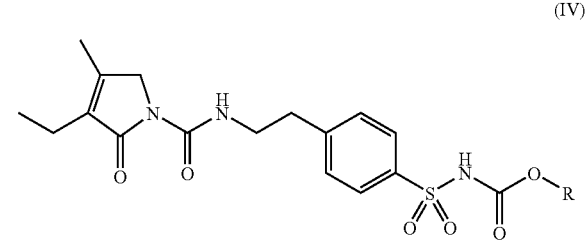

wherein R is a $C_1$-$C_5$ alkyl, giving glimepiride of formula I.

2. The method according to claim 1 wherein the trans-4-methylcyclohexylamine pivalate of formula VII has been obtained by reaction of trans-4-methylcyclohexylamine or of its salt with pivalic acid or its salt.

3. The method according to claim 2 wherein re-crystallized pivalate of formula VII is used.

4. The method according to claim 3 wherein the pivalate of formula VII has been re-crystallized from a solvent selected from the group consisting of $C_5$ to $C_8$ aliphatic hydrocarbons, cyclic hydrocarbons, aromatic hydrocarbons, and mixtures thereof.

5. The method according to claim 4 wherein the pivalate of formula VII has been re-crystallized from a solvent selected from the group consisting of hexane, heptane, cyclohexane toluene, and mixtures thereof.

6. The method according to claim 4, wherein the pivalate of formula VII has been re-crystallized from a solvent with at least one added co-solvent selected from the group consisting of $C_1$ to $C_5$ alcohols and $C_1$ to $C_5$ acid esters of $C_1$ to $C_5$ alcohols.

7. The method according to claim 5 wherein the pivalate of formula VII has been re-crystallized from a mixture of toluene and cyclohexane in a volume ratio of 1:3.

8. The method according to claim 1 wherein the pivalate of formula VII has been obtained by reaction of trans-4-methylcyclohexylamine or of its salt with pivalic acid or its salt, said trans-4-methylcyclohexylamine or its salt having been obtained from re-crystallized pivalate of formula VII by reaction with a base.

9. The method according to claim 8 wherein said trans-4-methylcyclohexylamine has been obtained from the pivalate of formula VII, re-crystallized from a mixture of toluene and cyclohexane in a volume ratio of 1:3.

10. The method according to claim 1, wherein a compound of general formula IV is used wherein R is methyl.

11. The method according to claim 1, wherein a compound of general formula IV is used wherein R is ethyl.

12. The method according to claim 1, wherein the glimepiride is purified via repeated boiling in toluene.

13. The method according to claim 12 wherein the glimepiride is purified via triple boiling in toluene.

14. The method according to claim 1, wherein the glimepiride is purified via crystallization from a solvent selected from the group consisting of dioxan, tetrahydrofuran, dimethoxyethane, diethoxymethane, acetic acid, dimethylsulfoxide, their mutual mixtures and mixtures with addition of acetone, acetonitrile or dimethylformamide.

15. The method according to claim 1, wherein the glimepiride is purified via stirring with a mixture of dimethylsulfoxide and acetonitrile at a temperature of 0 to 80° C.

16. Trans-4-Methylcyclohexylamine pivalate of formula VII

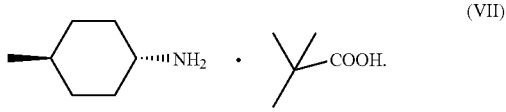

17. The method according to claim 2 wherein a compound of general formula IV is used wherein R is methyl.

18. The method of claim 6, further comprising adding water up to 50%.

* * * * *